(12) United States Patent
Flossmann et al.

(10) Patent No.: US 11,918,294 B2
(45) Date of Patent: Mar. 5, 2024

(54) VIRTUAL TRAJECTORY PLANNING

(71) Applicant: Brainlab AG, Munich (DE)

(72) Inventors: Sven Flossmann, Feldkirchen (DE); Sebastian Stopp, Munich (DE); Susanne Hager, Munich (DE); Christian Schmaler, Munich (DE); Christoffer Hamilton, Aschheim (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 17/298,330

(22) PCT Filed: Jan. 31, 2019

(86) PCT No.: PCT/EP2019/052314
§ 371 (c)(1),
(2) Date: May 28, 2021

(87) PCT Pub. No.: WO2020/156667
PCT Pub. Date: Aug. 6, 2020

(65) Prior Publication Data
US 2022/0096158 A1   Mar. 31, 2022

(51) Int. Cl.
*A61B 34/10*   (2016.01)
*G06T 19/00*   (2011.01)
(Continued)

(52) U.S. Cl.
CPC .............. *A61B 34/10* (2016.02); *G06F 3/013* (2013.01); *G06T 7/0012* (2013.01); *G06T 7/20* (2013.01);
(Continued)

(58) Field of Classification Search
CPC .............. A61B 34/10; A61B 2034/105; A61B 2034/107; A61B 2090/365; A61B 2090/371; G06T 7/70
(Continued)

(56) References Cited

U.S. PATENT DOCUMENTS 10,058,396 B1 *  8/2018  Genova .................. A61B 34/74
2014/0104274 A1 * 4/2014  Hilliges ................. G06F 3/017
345/424

(Continued)

FOREIGN PATENT DOCUMENTS

WO   WO-2018162079 A1 *  9/2018  ............. A61B 34/10
WO   WO-2018171880 A1 *  9/2018  ........... G06T 7/0016

OTHER PUBLICATIONS

International Search Report and Written Opinion for corresponding international application No. PCT/EP2019/052314, dated Oct. 28, 2019. 12 pages.
(Continued)

*Primary Examiner* — Javid A Amini
(74) *Attorney, Agent, or Firm* — Tucker Ellis LLP

(57) ABSTRACT

Provided is a method that encompasses the determination of a virtual trajectory within a virtual representation of a patient's anatomy, wherein the trajectory is defined by a user's visual axis relative to the three-dimensional virtual representation of the patient's anatomy. The method includes acquiring image data which describes the three-dimensional virtual representation of the patient's body part, acquiring position data which describes a spatial position of a user's visual axis within a virtual-world co-ordinate system, determining visualization data based on the image data and the position data, and determining virtual-world trajectory data based on the position data.

20 Claims, 3 Drawing Sheets

(51) Int. Cl.
    *G06F 3/01*         (2006.01)
    *G06T 7/70*         (2017.01)
    *G06T 7/00*         (2017.01)
    *G06T 7/20*         (2017.01)
    *A61B 90/00*      (2016.01)

(52) U.S. Cl.
    CPC .............. *G06T 7/70* (2017.01); *G06T 19/006* (2013.01); *A61B 2034/105* (2016.02); *A61B 2034/107* (2016.02); *A61B 2090/365* (2016.02); *A61B 2090/372* (2016.02)

(58) Field of Classification Search
    USPC ....................................................... 345/633
    See application file for complete search history.

(56) References Cited

U.S. PATENT DOCUMENTS

| | | | | |
|---|---|---|---|---|
| 2014/0184496 | A1* | 7/2014 | Gribetz | G06F 3/0482 345/156 |
| 2015/0302166 | A1* | 10/2015 | Thomson | G16H 50/50 703/2 |
| 2016/0225192 | A1* | 8/2016 | Jones | A61B 34/20 |
| 2016/0324580 | A1* | 11/2016 | Esterberg | A61B 34/10 |
| 2017/0165027 | A1* | 6/2017 | Paulson | G06F 3/013 |
| 2017/0258526 | A1* | 9/2017 | Lang | H05K 999/99 |
| 2017/0348056 | A1* | 12/2017 | Steinle | A61B 34/30 |
| 2018/0098812 | A1* | 4/2018 | Ootsuki | A61B 90/37 |
| 2018/0303558 | A1* | 10/2018 | Thomas | A61B 34/20 |
| 2019/0228859 | A1* | 7/2019 | Moctezuma de la Barrera | H04N 23/00 |
| 2019/0274523 | A1* | 9/2019 | Bates | G06T 7/97 |
| 2021/0228308 | A1* | 7/2021 | Berger | G06T 7/521 |
| 2021/0330250 | A1* | 10/2021 | Redmond | A61B 90/06 |
| 2021/0386503 | A1* | 12/2021 | Healy | G16H 50/20 |
| 2022/0151705 | A1* | 5/2022 | Nikou | A61B 90/361 |
| 2022/0160443 | A1* | 5/2022 | Spykerman | G06N 3/045 |

OTHER PUBLICATIONS

Shamir et al., "Trajectory planning with Augmented Reality for improved risk assessment in image-guided keyhole neurosurgery", Mar. 2011. 5 pages.

Esteves et al., "SmoothMoves: Smooth Pursuits Head Movements for Augmented Reality". Oct. 2017. 12 Pages.

\* cited by examiner

VIRTUAL TRAJECTORY PLANNING

RELATED APPLICATION DATA

This application is a national phase application of International Application No. PCT/EP2019/052314, filed Jan. 31, 2019, the contents of which are incorporated herein by reference.

FIELD OF THE INVENTION

The present invention relates to a computer-implemented method for determining a virtual medical trajectory for surgery or radiotherapy with respect to a virtual representation of a patient's body part, a corresponding computer program, a program storage medium storing such a program and a computer for executing the program, as well as a medical system comprising an electronic data storage device and the aforementioned computer.

TECHNICAL BACKGROUND

Prior to performing a minimally invasive surgical procedure that involves a placement of elongated instruments such as biopsy needles or infusion catheters, trajectories along which those instruments are advanced through body tissue have to be planned in order to avoid that advancing these instruments causes harm to critical anatomical structures between the entry point on the skin of the patient and a final target position where the tip of the instrument is to be placed at least temporarily. In a similar manner, trajectories for radiation beams generated for irradiating a target are planned prior to radiotherapy, wherein the trajectory is placed such that it does not intersect with anatomical structures that would be harmed by radiation.

Known approaches of planning such trajectories involve displaying 2D- or 3D-images and/or 2D- or 3D-image reconstructions of the patient's anatomy on which the planned procedure is to be performed, wherein medical personnel defines a later trajectory on the screen by using a computer mouse or similar input device.

Such procedures however demand a profound spatial sense from medical personnel.

It is object of the present invention to overcome the deficiencies of the prior art and to provide an easy to use and easy to understand approach of defining a medical trajectory within a patient's anatomy.

The present invention can be used in connection with any navigation procedure e.g. in connection with a system for radiotherapy such as ExacTrac®, or a system for image-guided surgery such as Kick® or Curve™, all of which being products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses the determination of a virtual trajectory within a three-dimensional virtual representation of a patient's anatomy, wherein the trajectory is defined by a user's visual axis relative to the virtual representation of the patient's anatomy.

GENERAL DESCRIPTION OF THE INVENTION

In this section, a description of the general features of the present invention is given for example by referring to possible embodiments of the invention.

The present invention reaches the aforementioned object by providing, in a first aspect, a computer-implemented medical method of determining a virtual medical trajectory with respect to a three-dimensional virtual representation of a patient's body part, wherein the method comprises the following steps:
  a) image data is acquired which describes the three-dimensional virtual representation of the patient's body part;
  b) position data is acquired which describes a spatial position of a user's visual axis within a virtual-world co-ordinate system;
  c) visualization data is determined based on the image data and the position data, which describes an image of the virtual representation of the patient's body part as seen along the user's visual axis within the virtual-world co-ordinate system, and
  d) virtual-world trajectory data is determined based on the position data, which describes the spatial position of the virtual trajectory with respect to the virtual representation of the patient's body part within the virtual-world co-ordinate system, wherein the spatial position of the virtual trajectory is defined by the spatial position of the user's visual axis within the virtual-world co-ordinate system.

In other words, the method according to the present invention may begin with receiving a 3D-image representation of the patient's anatomy a medical procedure is planned to be performed on. This data may encompass a three-dimensional image data set, wherein this data set may further be segmented with the help of an anatomical atlas for identifying particular anatomical structures within the image data set. The image data may be acquired from any suitable source, e.g. a CT-imaging device, a MR-imaging device or any other device for tomography.

Moreover, the spatial position (spatial location and/or spatial orientation) of the viewing axis of a person who is intended to plan the trajectory is determined. For example, this may be achieved by a conventional tracking system which tracks the user's head or eyes over time in real space. For example, such tracking system may comprise two or more cameras that detect tracking markers which are invariantly coupled to the user's head, such that the initial spatial position of the head and any subsequent movement is observed by the system. In the alternative or even additionally, a suitable tracking system may also comprise sensors (e.g. cameras, accelerometers and/or gyroscopes) which are coupled to the patient's head and therefore track the user's head by determining the spatial position and motion of stationary objects in the vicinity of the user (e.g. stationary medical appliances, walls and ceiling of an operating theater or similar objects) so as to eventually track the user's head position over time. Further, the spatial position of the user's eyes with respect to the user's head may be determined with the help of one or more video cameras observing the user's eyes, wherein such cameras may be invariantly coupled to the user's head.

Once the three-dimensional representation of the patient's anatomy together with the spatial position of the user's viewing direction is known, it is possible to calculate the spatial position of the user's viewing direction with respect to the virtual representation within a common co-ordinate system. For example, such virtual co-ordinate system can be rigidly coupled to the real world such that a virtual representation which remains stationary within the virtual world co-ordinate system will also remain stationary within the real world and a corresponding real-world co-ordinate system. However, it is also conceivable that such virtual world co-ordinate system can be positionally altered with respect to the real world such that a virtual representation that remains stationary within the virtual-world co-ordinate system moves with respect to the real world as the virtual world co-ordinate system is moved with respect to the real world.

With the above data acquired, a display image can be calculated, which shows how the virtual representation of the patient's anatomy is seen along the determined viewing axis of the user, including the distance between the user's eyes and the virtual representation, that has been calculated form the spatial position of the user's head determined by the tracking system.

In accordance with the present invention, the virtual trajectory is planned on the basis of the determined spatial position of the user's viewing direction and will therefore "follow" the user's head and/or eye movements to always coincide with the viewing axis of the user. If the user for example looks "past" certain anatomical structures shown in the virtual image and towards a target anatomical structure shown in the virtual image, the to be planned trajectory also extends past those structures towards the target anatomical structure. At this stage, the user can alter the position of the trajectory by moving the eyes and/or the head with respect to the virtual image representation of the patient's anatomy. As soon as the trajectory reaches a desired position, the user is then able establish the spatial position of the trajectory with respect to the virtual representation of the patient's anatomy by a user input, for example by pressing a button, performing a gesture or any other suitable command.

Further, after a desired position of the to be planned trajectory has been established, the virtual representation of the patient's anatomy together with a virtual representation of the trajectory may then also be observed from any other spatial direction so as to verify a proper placement of the trajectory.

In a further embodiment that goes beyond the above planning procedure, the spatial position of a "real" medical trajectory is determined with respect to the patient's actual body part. Thus, the described method can further encompass the following steps:
e) transformation data is determined which describes a transformation between the virtual-world co-ordinate system and a real-world co-ordinate system;
f) real-world trajectory data is determined based on the virtual-world trajectory data and the transformation data, which describes the spatial position of the real trajectory within a real-world co-ordinate system and with respect to the patient's actual body part registered with the virtual representation of the patient's body part.

In other words, the spatial data that has been calculated within the virtual world co-ordinate system is transferred into the co-ordinate system that corresponds to the real-world, i.e. is stationary within the real-world.

Thus, the spatial position of the actual trajectory for a radiation beam or for advancing an instrument within the patient's body is calculated from the spatial position of the virtual trajectory which has been established within the virtual world.

As can be seen from the above, an actual medical trajectory is planned in an easy to understand manner via a three-dimensional virtual representation of the patient's anatomy, which is displayed to the user via a suitable display device. After a desired spatial position of the virtual trajectory with respect to the virtual representation of the patient's anatomy has been reached and established, the positional data describing the desired trajectory position is transferred from the virtual-world co-ordinate system assigned to the virtual world to a real-world co-ordinate system assigned to the real-world of the actual anatomy of the patient and the actual trajectory along which a radiation beam will extend or an instrument will be advanced so as to reach a desired medical outcome (e.g. delivering a liquid substance to or removing tissue from a target location within the anatomy with an elongated instrument while critical anatomical structures are not harmed by advancing the instrument).

In accordance with a further example of the invention, the spatial position of the virtual representation of the patient's body part remains invariant with respect to the real-world co-ordinate system for at least a defined amount of time, and wherein the spatial position of the virtual trajectory within the virtual-world co-ordinate system is modified by changing the spatial position of the viewing axis within the virtual-world co-ordinate system.

As already described further above, this results in a virtual anatomy which remains stationary in the real-world, i.e. in a planning or operating theater where a later surgical procedure is planned. Thus, the user may simply adjust the relative position of the virtual trajectory by moving relative to/walking around the virtual representation that is displayed to the user. Of course, this may involve one or more positional adjustments by which the otherwise stationary virtual representation is moved to a desired location and/or into a desired orientation which are more convenient for the user to establish a trajectory position. For example, it may be impossible to establish a trajectory in a vertical direction with respect to an upright virtual representation that is displayed to the user at eyelevel. Thus, the user may adjust the spatial position by any suitable user input and lower its position or rotate it by a certain amount so that it is possible for the user to look at the structure and establish the trajectory in the vertical direction. After such positional adjustment, the virtual representation remains stationary again with respect to the real-world co-ordinate system.

Further, the spatial position of the virtual representation of the patient's body part may also be adjustable with respect to the real-world co-ordinate system, wherein the spatial position of the virtual trajectory within the virtual world co-ordinate system is modified by changing the spatial position of the virtual representation of the patient's body part with respect to the real-world co-ordinate system. Thus, the spatial position of the virtual anatomical representation may be fully adjustable over time, such that the user does not need to move his/her head for adjusting the trajectory position with respect to the anatomy, but rather may sit/stand still and adjust the trajectory position by simply relocating/rotating the virtual anatomy in front of him/her. Just like the aforementioned example for adjusting the position of the virtual representation, this may be done by a "grasping" gesture by which the virtual representation follows the user's hands grasping the virtual representation in the real-world.

Even though the virtual representation of the patient's body part may initially be displayed at any arbitrary location in the real-world, at least an initial display at dedicated locations and/or orientations is preferred, such that the start of the planning procedure is predictable. For example, the display may always start with an "upright" orientation of the virtual anatomy, with the cranial-caudal direction of the anatomy being parallel to the vertical (Y) axis of the real-world co-ordinate system. Further, the initial position for the display may be disposed at a dedicated location within a planning or operating theater. For example, the planning procedure may start off with the virtual representation being displayed "registered" with the actual anatomy of a patient, i.e. with the location and/or orientation and/or size of the virtual representation being the same as of the corresponding real anatomy within the planning or operating theater. Thus, the virtual representation of the patient's body part within the virtual world co-ordinate system is, and in particular remains superimposed with the patient's actual body part within the real-world co-ordinate system for at least a defined amount of time.

Any of the above examples for the inventive computer-implemented medical method may be performed by using any conceivable and suitable display device that optically presents the calculated data to the user. Specifically, the image described by the visualization data is shown to the user via a head-mounted display-device, particularly AR-spectacles or VR-goggles, specifically wherein the visual axis is derived from an optical axis of a head-mounted display-device or an optical axis of at least one eye of the user.

Implementing the invention by using AR-spectacles or VR-goggles has the advantage over using portable consumer devices such as tablet computers or smartphones, that the user gets the most realistic impression that the virtual representation of the patient's body part is actually present in the planning or operating theater.

According to a further example of the present invention, the visualization data describes the image of the virtual representation of the patient's body part as seen along the user's visual axis
a) from outside the virtual representation of the patient's body part, and/or
b) from inside the virtual representation of the patient's body part, particularly wherein the virtual representation of the patient's body part is enlarged to surround the user's position within the virtual-world co-ordinate system.

In case the trajectory has to take a rather difficult pathway from the entry point of the patient's anatomy to the target location, it may be beneficial to provide both the above possibilities, so that the user may, for example establish the desired trajectory by viewing onto the patient's anatomy from outside the anatomy, and then, afterwards, verify a correct and desired trajectory position by viewing along the trajectory in the opposing direction, i.e. from inside the patient's anatomy, or vice versa. In a specific example, the user may also take the position of the target location within the patient's virtual anatomy and look to the outside from there to find the best possible pathway for the later trajectory.

Further, the image described by the visualization data includes a visualization of the virtual trajectory, particularly wherein the image described by the visualization data indicates whether a structure of the virtual representation of the patient's body part is hit by the virtual trajectory. Visualizing the virtual trajectory within the virtual representation, particularly after the trajectory position has been established, makes it easy for the user to verify that the trajectory is/has been positioned as desired with respect to possible critical structures. Further, indicating whether or not structures, particularly critical structures, are hit or crossed by the trajectory, for example by highlighting hit/crossed structures, helps in avoiding that the user does not recognize unintended intersections of the trajectory with anatomical structures.

Additionally or alternatively, the image described by the visualization data may also indicate a distance between a structure of the virtual representation of the patient's body part and the trajectory. For example, a value may be shown for the closest distance between the trajectory and a certain anatomical structure, or the anatomical structure in question may be dyed in different colors corresponding to the distance, such as green for uncritical distances, yellow for critical distances and red for an intersection between the trajectory and the structure.

Further, the image described by the visualization data may also indicate at least one of a forbidden zone for the virtual trajectory and a forbidden parameter of the virtual trajectory, which is/are defined by limitations of a later surgical or therapeutic procedure. For example, forbidden entry regions can be defined or outlined by the user beforehand and are therefore not available for the trajectory to enter the patient's anatomy. Further, one or more regions or volumes within the patient's anatomy may be defined, as well, which cannot be crossed by the trajectory afterwards. In this regard it may be possible that a warning signal is output as soon as the trajectory intersects with a forbidden zone or volume, or that it is not even possible to place a trajectory through such region or volume in the first place.

According to a further example, further parameters of the virtual trajectory are selected, particularly after a desired spatial position of the virtual trajectory with respect to the virtual representation of the patient's body part has been established and/or wherein the further parameters are modified via gesture control, specifically via head movements.

For example, the width of the trajectory may be adjusted by the user when moving the head, particularly along an already established trajectory, towards or away from the target region or any other suitable location, with the trajectory widening up or narrowing, respectively.

In a further example, a desired spatial position and/or a desired parameter of at least one virtual trajectory is selected via gesture control, particularly via an eye gesture control. In a specific example, the user may establish a desired trajectory by blinking with one or both eyes. Any other suitable gesture which does not necessitate head movements is however is also conceivable, for example voice control or hand gestures.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a computer-readable program storage medium on which the program according to the second aspect is stored. The program storage medium is for example non-transitory.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
  a) the at least one computer according to the fourth aspect;
  b) at least one electronic data storage device storing at least the trajectory data and/or image data;
  c) a display device displaying at least the visualization data to a user,
    wherein the at least one computer is operably coupled to
      the at least one electronic data storage device for acquiring, from the at least one data storage device, at least the trajectory data, and/or the image data, and
      the display device for issuing a control signal to the display device for controlling the operation of the display device on the basis of the trajectory data and/or image data.

Alternatively or additionally, the invention according to the fifth aspect is directed to a for example non-transitory computer-readable program storage medium storing a program for causing the computer according to the fourth aspect to execute the data processing steps of the method according to the first aspect.

The invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to a planning procedure. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate system. The data can be multiple photographs and/or data from different sensors, different times or different viewpoints. It is used in computer vision, medical imaging and in compiling and analyzing images and data from satellites. Registration is necessary in order to be able to compare or integrate the data obtained from these different measurements.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
a computer for processing the absolute point data and the relative point data;
a detection device for detecting the position of the main and auxiliary points in order to generate the absolute point data and to supply the absolute point data to the computer;
a data interface for receiving the relative point data and for supplying the relative point data to the computer; and
a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the center of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational center of the femur when moved relative to the acetabulum.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

The present invention makes use of display methods that are widely known as "augmented reality" or "virtual reality". While the first intends to provide, by the use of portable consumer devices such as tablet computers or smartphones, or spectacles worn by the user/viewer, a (semitransparent) overlay over the user's/viewer's natural field of view perceived by the eyes that receive light in the visual spectrum which is emitted, transmitted and/or reflected from objects within the user's/viewer's field of view, the latter is to provide a fully artificial environment without any "natural light" from the natural environment being received by the user's/viewer's eyes.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
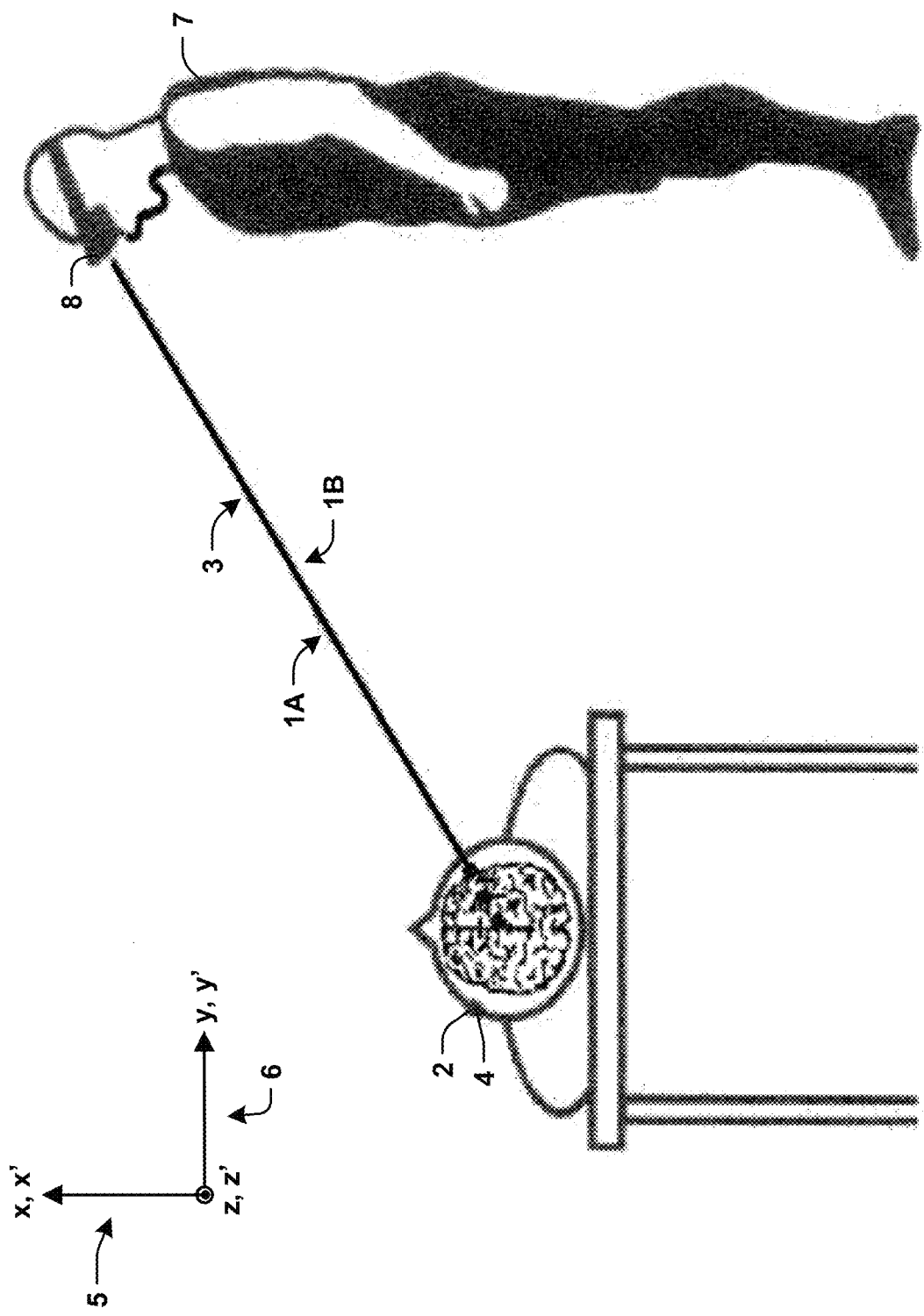
FIG. 1 shows a first example of the invention with the virtual world co-ordinate system coinciding with the real-world co-ordinate system.

FIG. 1 shows a first example for implementing the inventive method within a planning or operating theater: The user 7 wears AR-spectacles 8 that allow him to visually see the natural environment, including the actual body part 2 of the patient who takes supine posture on a patient couch (not indicated).

A real-world co-ordinate system 5 defining the axes X, Y and Z is assigned to the real-world and the actual patient's body part 2, wherein a later real trajectory 1B is positionally defined within co-ordinate system 5 on the basis of the position of a virtual trajectory 1A within a virtual world co-ordinate system 6 defining the axes X', Y' and Z'. On the basis of a three-dimensional data set of the patient's anatomy 2, a virtual representation 4 of the patient's actual body part 2 is calculated and positioned within the virtual world co-ordinate system 6 at the exact same position as the actual body part 2. The real-world co-ordinate system 5 coincides with the virtual world co-ordinate system 6. Since the AR-spectacles 8 are tracked in space by a tracking system (not shown), the user's visual axis 3 which coincides with the optical axis of the AR-spectacles, the spatial position (spatial location and spatial orientation) of the user's visual axis 3 can be calculated within the real-world co-ordinate system 5 but also within the virtual world co-ordinate system 6 coinciding therewith.

Based on the above obtained data, the AR-spectacles 8 can provide an image to the user 7 that has been calculated from the three-dimensional virtual representation 4 of the patient's body part together with the relative position of the viewing axis 3 (in particular the viewing position of the user's eyes) with respect to the three-dimensional virtual representation 4, such that the image shows the virtual representation 4 in such a manner that the user 7 gets the impression that the virtual representation 4 perfectly matches with the actual body part 2.

In order to adjust the position of the virtual trajectory 1A with respect to the virtual representation 4, the user 7 may simply change his/her position with respect to the patient's anatomy 2 and look at it from another direction, but also from a closer/more distant position. The position of the virtual trajectory 1A then changes correspondingly. As soon as the user 7 deems the spatial position of the virtual trajectory 1A desirable, he/her performs an eye gesture by blinking one or both eyes which will establish the position of the virtual trajectory within the virtual world co-ordinate system 6.

In order to transfer the relative position between the virtual trajectory 1A with respect to the virtual representation 4 of the patient's body part within the virtual world co-ordinate system 6 into the real-world co-ordinate system 5 so as to determine the desired relative position between the actual body part 2 and actual trajectory 1B for advancing an instrument later on, the embodiment shown in FIG. 1 does not need any transformation by a transformation matrix, since co-ordinate systems 5 and 6 already coincide with each other.

Figure 2:
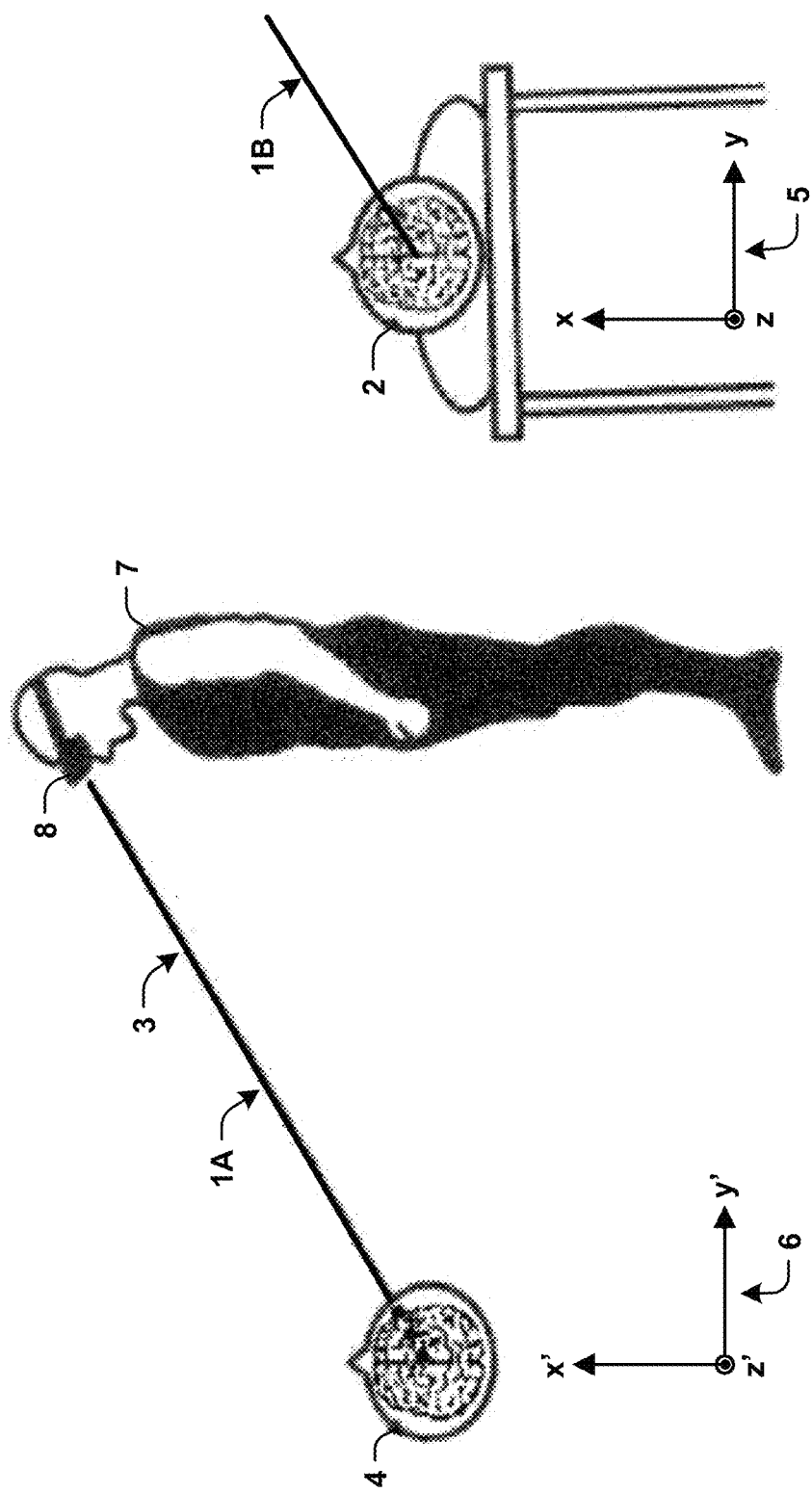
FIG. 2 shows a second example of the invention with the virtual world co-ordinate system (being different/adjustable) with respect to the real-world co-ordinate system.

Such transformation is however necessary for the second embodiment shown in FIG. 2. Since co-ordinate systems 5 and 6 are different from each other, a transformation matrix has to be calculated such that a transformation of positional data from the virtual world co-ordinate system 6 into the real-world co-ordinate system 5 is possible. On the other hand, the inventive planning procedure can be performed at any desired place remote from the patient. Further, the spatial location and/or spatial orientation of the virtual representation 4 can be altered as desired by the user 7, such that it is more convenient to establish a desired trajectory position with respect to the patient's anatomy.

Figure 3:
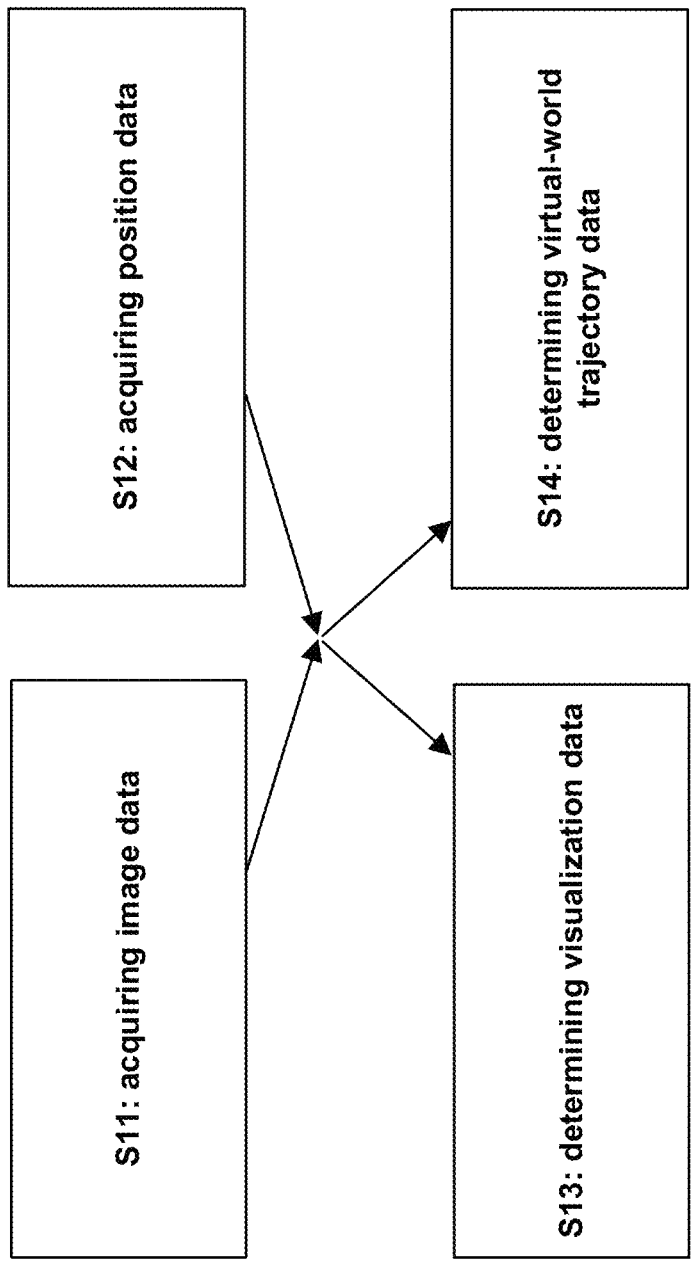
FIG. 3 shows the basic steps of the inventive method.

FIG. 3 shows the basic steps of the inventive method, wherein both, the visualization data and the virtual world trajectory data is calculated from the acquired image data and the acquired position data describing a three-dimensional virtual representation of the patient's body part and a spatial position of the user's visual axis within a virtual world co-ordinate system, respectively.

Further disclosed herein is a system according to the present invention, comprising a computer on which a program is run such that the computer can perform any of the description embodiment of the inventive method, particularly the basis method steps as shown in FIG. 3. On the one hand, computer is connected to a data storage device that may store the image data acquired from the patient as well as the tracking data which allows to determine the spatial position of the AR-spectacles together with the optical axis thereof. Additionally, the computer is connected to the AR-spectacles such that data required for displaying at least the visualization data to the user 7.

The invention claimed is:

1. A computer-implemented method of determining a virtual trajectory with respect to a three-dimensional virtual representation of a patient's body part, the method comprising:
   a) acquiring image data which describes the three-dimensional virtual representation of the patient's body part;
   b) acquiring position data which describes a spatial position of a user's visual axis within a virtual-world co-ordinate system;
   c) determining visualization data based on the image data and the position data, which describes an image of the virtual representation of the patient's body part as seen along the user's visual axis within the virtual-world co-ordinate system; and
   d) determining virtual-world trajectory data based on the position data, which describes the spatial position of the virtual trajectory with respect to the virtual representation of the patient's body part within the virtual-world co-ordinate system, wherein the spatial position of the virtual trajectory within the virtual-world co-ordinate system is defined to coincide with and to move with the spatial position of the user's visual axis as the user's visual axis is moved within the virtual-world co-ordinate system until the spatial position of the virtual trajectory within the virtual-world co-ordinate system is fixed to a specific spatial position with respect to the virtual representation of the patient's body part via a user input.

2. The method according to claim 1, wherein a real trajectory is determined with respect to a patient's actual body part, wherein the method further comprises:

e) determining transformation data which describes a transformation between the virtual-world co-ordinate system and a real-world co-ordinate system; and f) determining real-world trajectory data based on the virtual-world trajectory data and the transformation data, which describes the spatial position of the real trajectory within the real-world co-ordinate system and with respect to the patient's actual body part registered with the virtual representation of the patient's body part.

3. The method according to claim 2, wherein the spatial position of the virtual representation of the patient's body part remains invariant with respect to the real-world co-ordinate system for at least a defined amount of time, and wherein the spatial position of the virtual trajectory within the virtual-world co-ordinate system is modified by changing the spatial position of the user's visual axis within the virtual-world co-ordinate system.

4. The method according to claim 2, wherein the spatial position of the virtual representation of the patient's body part is adjustable with respect to the real-world co-ordinate system, and wherein the spatial position of the virtual trajectory within the virtual-world co-ordinate system is modified by changing the spatial position of the virtual representation of the patient's body part with respect to the real-world co-ordinate system.

5. The method according to claim 2, wherein the virtual representation of the patient's body part within the virtual-world co-ordinate system is superimposed with the patient's actual body part within the real-world co-ordinate system for at least a defined amount of time.

6. The method according to claim 1, wherein the image described by the visualization data is shown to the user via a head-mounted display-device.

7. The method according to claim 6, wherein the visual axis is derived from an optical axis of the head-mounted display-device or an optical axis of at least one eye of the user.

8. The method according to claim 1, wherein the visualization data describes the image of the virtual representation of the patient's body part as seen along the user's visual axis from at least one of:
a) from outside the virtual representation of the patient's body part, and
b) from inside the virtual representation of the patient's body part.

9. The method according to claim 8, wherein the visualization data describes the image of the virtual representation of the patient's body part as seen along the user's visual axis from inside the virtual representation of the patient's body part, wherein the virtual representation of the patient's body part is enlarged to surround the user's position within the virtual-world co-ordinate system.

10. The method according to claim 1, wherein the image described by the visualization data indicates at least one of a forbidden zone for the virtual trajectory and a forbidden parameter of the virtual trajectory, each of which is defined by limitations of a later surgical or therapeutic procedure, and wherein further parameters of the virtual trajectory are selected after a specific spatial position of the virtual trajectory with respect to the virtual representation of the patient's body part has been selected and/or wherein the further parameters are modified via gesture control.

11. The method according to claim 10, wherein the further parameters are modified via gesture control comprising head movements.

12. The method according to claim 1, wherein a specific spatial position and/or a specific parameter of at least one virtual trajectory is selected via gesture control comprising eye gesture control.

13. The method according to claim 1, wherein the image described by the visualization data includes a visualization of the virtual trajectory, and/or wherein the image described by the visualization data indicates whether a structure of the virtual representation of the patient's body part is hit by the virtual trajectory.

14. The method according to claim 1, wherein the image described by the visualization data indicates a distance between a structure of the virtual representation of the patient's body part and the virtual trajectory.

15. The method according to claim 1, wherein the spatial position of the virtual trajectory with respect to the virtual representation of the patient's body part within the virtual-world co-ordinate system is moved by:
(i) changing the user's viewing direction with respect to the virtual representation of the patient's body part within the virtual-world co-ordinate system, and/or
(ii) changing a distance of the user's viewing position with respect to the virtual representation of the patient's body part within the virtual-world co-ordinate system.

16. A non-transitory computer readable storage medium storing a program, that when executed on at least one processor of a computer or loaded onto the at least one processor of the computer, causes the computer to perform a method of determining a virtual trajectory with respect to a three-dimensional virtual representation of a patient's body part, the method comprising:
acquiring image data which describes the three-dimensional virtual representation of the patient's body part;
acquiring position data which describes a spatial position of a user's visual axis within a virtual-world co-ordinate system;
determining visualization data based on the image data and the position data, which describes an image of the virtual representation of the patient's body part as seen along the user's visual axis within the virtual-world co-ordinate system; and
determining virtual-world trajectory data based on the position data, which describes the spatial position of the virtual trajectory with respect to the virtual representation of the patient's body part within the virtual-world co-ordinate system, wherein the spatial position of the virtual trajectory within the virtual-world co-ordinate system is defined to coincide with and to move with the spatial position of the user's visual axis as the user's visual axis is moved within the virtual-world co-ordinate system until the spatial position of the virtual trajectory within the virtual-world co-ordinate system is fixed to a specific spatial position with respect to the virtual representation of the patient's body part via a user input.

17. A medical system, comprising:
a) at least one computer configured to:
acquire image data which describes a three-dimensional virtual representation of a patient's body part;
acquire position data which describes a spatial position of a user's visual axis within a virtual-world co-ordinate system;
determine visualization data based on the image data and the position data, which describes an image of a virtual representation of the patient's body part as seen along the user's visual axis within the virtual-world co-ordinate system; and determine virtual-world trajectory data based on the position data, which describes the spatial position of a virtual trajectory with respect to the virtual representation of the patient's body part within the virtual-world co-ordinate system, wherein the spatial position of the virtual trajectory within the virtual-world co-ordinate system is defined to coincide with and to move with the spatial position of the user's visual axis as the user's visual axis is moved within the virtual-world co-ordinate system until the spatial position of the virtual trajectory within the virtual-world co-ordinate system is fixed to a specific spatial position with respect to the virtual representation of the patient's body part via a user input;

b) at least one electronic data storage device storing at least one of the trajectory data and image data; and c) a display device displaying at least the visualization data to a user, wherein the at least one computer is operably coupled to the at least one electronic data storage device for acquiring, from the at least one electronic data storage device, at least one of the trajectory data and the image data, and the display device for issuing a control signal to the display device for controlling the operation of the display device on the basis of at least one of the trajectory data and the image data.

18. The medical system according to claim 17, wherein a real trajectory is determined with respect to a patient's actual body part, wherein the at least one computer is further configured to:

determine transformation data which describes a transformation between the virtual-world co-ordinate system and a real-world co-ordinate system; and determine real-world trajectory data based on the virtual-world trajectory data and the transformation data, which describes the spatial position of the real trajectory within the real-world co-ordinate system and with respect to the patient's actual body part registered with the virtual representation of the patient's body part.

19. The medical system according to claim 17, wherein the image described by the visualization data includes a visualization of the virtual trajectory, and/or wherein the image described by the visualization data indicates whether a structure of the virtual representation of the patient's body part is hit by the virtual trajectory.

20. The medical system according to claim 17, wherein the visualization data describes the image of the virtual representation of the patient's body part as seen along the user's visual axis from at least one of:

a) from outside the virtual representation of the patient's body part, and b) from inside the virtual representation of the patient's body part.

* * * * *